(12) United States Patent
Matsuura et al.

(10) Patent No.: US 7,144,385 B2
(45) Date of Patent: Dec. 5, 2006

(54) DISCHARGING IMPLEMENT FOR MEDICAL CARE

(75) Inventors: Yoshifumi Matsuura, Koriyama (JP); Tomohiro Isono, Akita (JP); Yukihiko Sakaguchi, Akita (JP)

(73) Assignee: Sumitomo Bakelite Company Limited, Tokyo (JP)

(*) Notice: Subject to any disclaimer, the term of this patent is extended or adjusted under 35 U.S.C. 154(b) by 210 days.

(21) Appl. No.: 10/497,214

(22) PCT Filed: Jun. 18, 2002

(86) PCT No.: PCT/JP02/06056

§ 371 (c)(1),
(2), (4) Date: May 28, 2004

(87) PCT Pub. No.: WO03/045470

PCT Pub. Date: Jun. 5, 2003

(65) Prior Publication Data

US 2005/0080387 A1    Apr. 14, 2005

(30) Foreign Application Priority Data

Nov. 29, 2001  (JP) .............................. 2001-363577

(51) Int. Cl.
*A61M 37/00* (2006.01)
*A61M 5/178* (2006.01)
*A61M 1/06* (2006.01)
*A61M 1/00* (2006.01)

(52) U.S. Cl. .......................... 604/132; 604/37; 604/75; 604/142; 604/153; 604/212; 604/213; 604/217; 604/540

(58) Field of Classification Search ................ 604/317, 604/319, 320, 323, 326, 327, 328, 315, 316, 604/540–544, 37, 75, 132, 133, 142, 153, 604/161, 164.01, 171, 212, 213, 216, 217; D24/118
See application file for complete search history.

(56) References Cited

U.S. PATENT DOCUMENTS

| | | | |
|---|---|---|---|
| 3,376,868 A | * | 4/1968 | Mondiadis .................. 604/133 |
| 3,421,504 A | * | 1/1969 | Gibbons ....................... 604/73 |
| 3,742,952 A | * | 7/1973 | Magers et al. .............. 604/133 |
| 3,800,795 A | | 4/1974 | Walker |

(Continued)

FOREIGN PATENT DOCUMENTS

EP    0 390 106 A2    10/1990

(Continued)

*Primary Examiner*—Tatyana Zalukaeva
*Assistant Examiner*—Michael G Bogart
(74) *Attorney, Agent, or Firm*—Smith, Gambrell & Russell

(57) ABSTRACT

For safely inserting a catheter into a chest cavity of a child or corpulent patient to be retained therein and for preventing atmospheric air from proceeding into the chest cavity during a removal of a penetrating needle, discharge equipment for medical procedures is provided which equipment includes a connector cap and a storage bottle detachably connectable to each other, a connector to be connected to the catheter retained in the patient, a check valve including an outer periphery covered by a protective cover and being openable only toward a storage bottle side, and a coupling device to the storage bottle mounted on the connector cap. The storage bottle is a hollow container including an inlet port and a discharge port, a detachably connecting device for the connector cap mounted on the inlet port, and a check valve openable only toward an exterior of the storage bottle is mounted on the discharge port.

15 Claims, 10 Drawing Sheets

U.S. PATENT DOCUMENTS

| | | | |
|---|---|---|---|
| 3,875,941 A * | 4/1975 | Adair | 604/540 |
| 3,991,763 A | 11/1976 | Genese | |
| 4,141,361 A * | 2/1979 | Snyder | 604/133 |
| 4,392,858 A * | 7/1983 | George et al. | 604/133 |
| 4,392,860 A * | 7/1983 | Huck et al. | 604/212 |
| 4,529,402 A * | 7/1985 | Weilbacher et al. | 604/133 |
| 4,578,060 A * | 3/1986 | Huck et al. | 604/133 |
| 4,643,719 A * | 2/1987 | Garth et al. | 604/73 |
| D312,132 S * | 11/1990 | Jaron | D24/118 |
| 5,318,548 A * | 6/1994 | Filshie | 604/319 |
| 5,318,550 A * | 6/1994 | Cermak et al. | 604/349 |

FOREIGN PATENT DOCUMENTS

| | | |
|---|---|---|
| JP | 61-90669 | 5/1986 |
| JP | 06-277295 | 10/1994 |
| JP | 08-224313 | 9/1996 |
| JP | 2001-218830 | 8/2001 |
| JP | 2004-16469 A * | 6/2004 |
| JP | 2004-229780 A * | 8/2004 |
| WO | WO 96/11031 | 4/1996 |

* cited by examiner

FIG.2
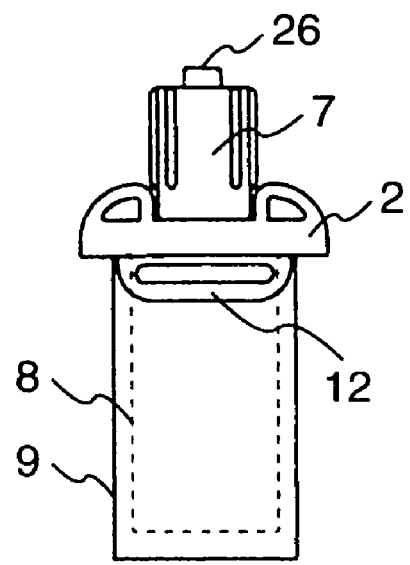
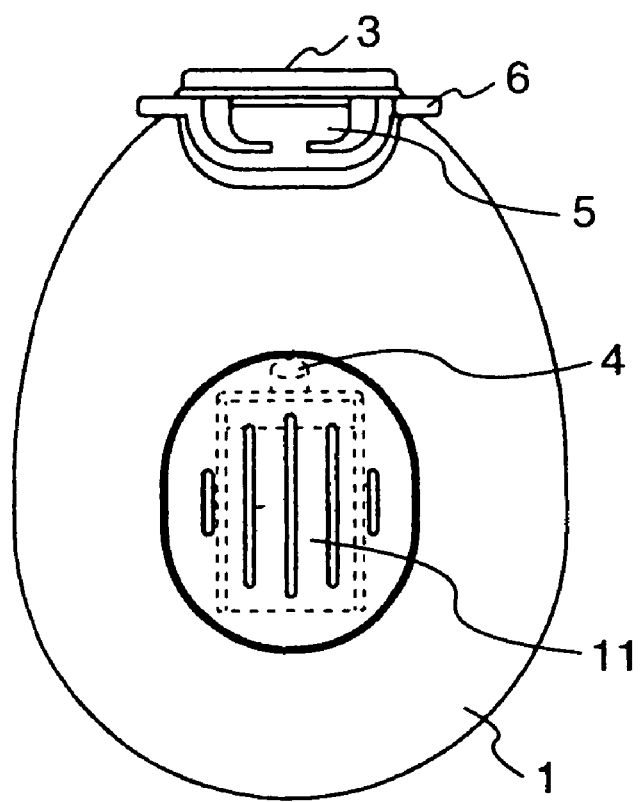

FIG.3
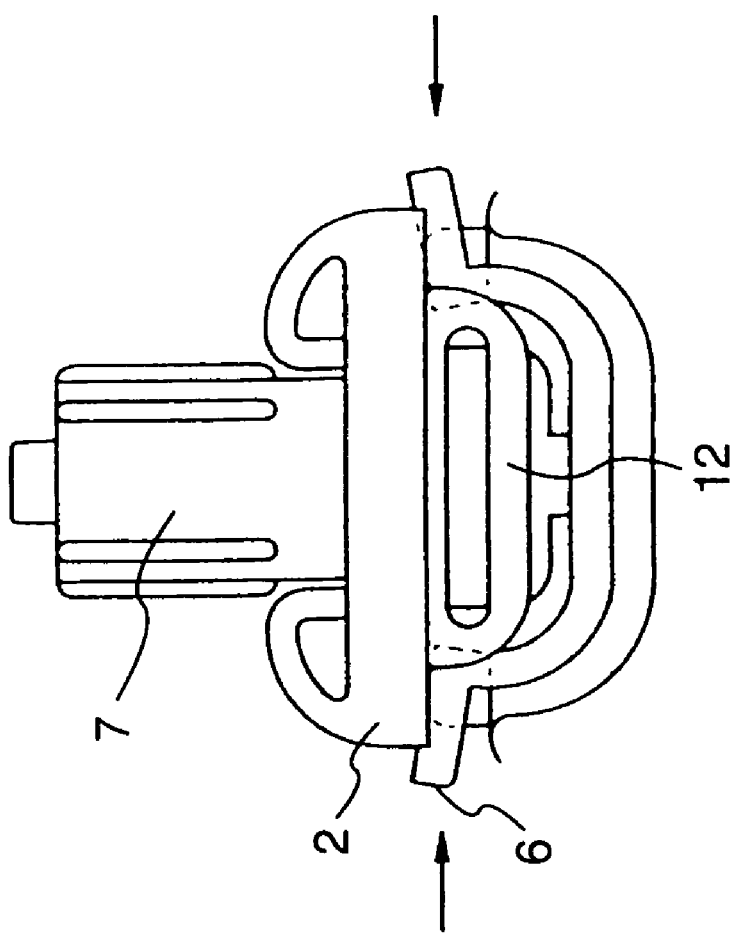
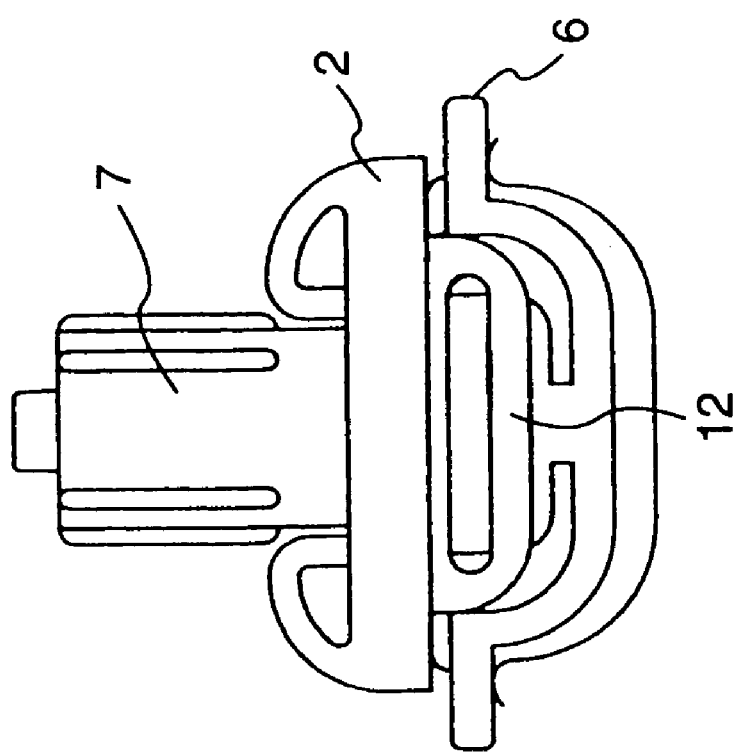

DISCHARGING IMPLEMENT FOR MEDICAL CARE

TECHNICAL FIELD

The present invention relates to discharging equipment for a medical procedure for discharging gas and liquid pooling in a chest cavity and abdominal cavity, and collecting the liquid.

A chest is continuously distensible by a negative pressure ($-5$~$-20$ cmH$_2$O) kept always in a normal chest cavity. If this condition is disturbed by a pneumothorax, external breast injury or the like, the chest cannot be distended sufficiently so that ventilation is affected. While in medical equipment for the medical treatment en of a body cavity, particularly the breast of a pneumothorax patient or the like, a catheter is positioned in the chest cavity and connected to a reservoir tank to discharge a liquid and gas, a method of using a container including a tubule connected to the catheter and sealed with water and an air inlet port at a vicinity of an upper part thereof, and a method of connecting a check valve kit as a so-called flatter valve to the catheter and connecting a bag or a bottle-shaped container to the check valve kit to collect the liquid are used.

Since in the former method, numerous operations and care are necessary for the water sealing of the container on supplying the water, preventing the water from being leaked, and preventing the water from moving upward in the tubule sealed with the water when the water height is increased by the discharge of the liquid, and a great size of the container is used for safety, equipment becomes inconvenient for portability. Since in the latter method, a complicated operation of connecting the check valve kit as the flatter valve to the container as the bag or the like is needed and the check valve kit and the bag or the like are arranged in series when being carried, its size is great and it is not suitable for portability.

In order to improve this, the applicant discloses for particularly improving the portability in JP-A-61-90669 an all-in-one kit in which the check valve is incorporated in the reservoir tank, and whereby basically, the operation is completed by connecting only the all-in-one kit after the catheter is positioned.

However, since a storage of the discharged liquid amount is considered for this all-in-one kit, the check valve is arranged above a container body, so that is has an excessively large size for a patient of pneumothorax with a small amount of the discharged liquid, and its downsizing is required. In another aspect, when using the prior art equipment including this all-in-one kit, further equipment for performing compulsory discharge of the air from a syringe, aspiration pump or the like needs to be used for quickly discharging the air from the chest cavity just after being connected to the patient and releasing a clog from the catheter, so that an excessive cost is necessary. Further, when the catheter of the prior art equipment is positioned in the abdominal cavity, a partial anesthesia is performed on a portion of a chest wall to be penetrated, the tissue is incised along a small length, the catheter is inserted, and a penetrating needle incorporated in the catheter is drawn out therefrom when a forward end of the catheter reaches inside of the chest cavity. In this situation, since atmospheric air proceeds into the chest cavity through the catheter, it is difficult for the negative pressure to be kept at the inside of the chest cavity, and a positioning operation necessarily should be done in an operating room with the clean atmospheric air. Further, as a problem with the insertion and penetration, there is a probability that the chest wall of small thickness of a small child is penetrated on the insertion and penetration, and there is a probability that the chest of a corpulent patient with a large thickness of the chest wall is penetrated because of difficulty in determining an arrival into the chest cavity.

DISCLOSURE OF THE INVENTION

A purpose of the invention is to solve these prior art problems, particularly to provide discharging equipment for a medical procedure in the case where an amount of discharged liquid is small, in which a size thereof is smaller, a manual operation for discharging can be performed by itself without using any other necessary equipment, the atmospheric air is prevented from proceeding into the chest cavity when the penetrating needle is drawn out, and the catheter can be safely inserted into and detained in the chest cavity with using additionally a cannula needle, a guide wire and a dilator when the catheter is inserted into a child or a corpulent patient.

That is, the inventions are, (1) a discharging equipment for medical procedure, including a storage bottle as a hollow container having an inlet port and a discharge port, wherein a check valve opening only in an inward direction for the storage bottle is arranged at the inlet port, and a check valve openable only in an outward direction is arranged at the discharge port, (2) a discharging equipment for medical procedure, including a connector cap and the storage bottle detachably connectable to each other, wherein a connector for connecting the catheter retained in the patient, the check valve opening only to a storage bottle side and having an outer periphery covered by a protect cover, and a connecting device to be connected to the storage bottle are mounted on the connector cap, and the storage bottle is the hollow container having the outlet port and the discharge port, a detachably connecting device to be connected to the connecting cap is mounted on the outlet port, and the check valve opening only in the outward direction of the storage bottle is arranged at the discharge port, (3) the discharging equipment for medical procedure as described (2), wherein when the connector cap is connected to the outlet port of the storage bottle, the protect cover of the check valve mounted on the connector cap is arranged in the storage bottle while being prevented from contacting an inner wall of the storage bottle, and a distance between the inner wall at a back face of the storage bottle and the protect cover is not less than 5 mm, (4) a discharging equipment for medical procedure, including a penetrating needle, a catheter and the storage bottle, wherein the penetrating needle is a small diameter needle including a connector at a back end thereof, the catheter has a tapered front end, an inner cavity into which the penetrating needle can be inserted, a plurality of side holes at a front end side thereof, and a penetrating needle insert port from the side holes toward a back end of the catheter, a check valve opening only in a direction toward the back end of the catheter and the connector cap with the connecting device are mounted on the back end of the catheter, and the storage bottle has the outlet detachably connectable to the connector cap at an upper portion thereof and the discharge port including a check valve opening only to the outside of the hollow container, (5) the discharging equipment for medical procedure as described (4), wherein the penetrating needle insert port has a notch, (6) the discharging equipment for medical procedure as described (4) or (5), wherein the penetrating needle is a double needle including an inner needle and an outer tubular needle, (7) the discharging equipment for medical procedure as described in any one of (1)–(6), wherein a connector to be connected to a suction source is mounted on an outlet of the check valve at the discharge port, (8) the discharging equipment for medical procedure as described in any one of (2)–(6), wherein an adapter with the connector to be connected to the suction source is detachably connectable to a check valve side of the connector cap, (9) the discharging equipment for medical procedure as described in any one of (2)–(8), wherein the detachably connecting device of the storage bottle and the outlet are included by an integrally formed element with a release lever, and the storage bottle and the connector cap are detachably connected to each other with a release of the connecting device of the connector cap by the release lever,

(10) the discharging equipment for medical procedure as described in any one of (1)–(10), wherein the storage bottle is made of an elastic body,

(11) the discharging equipment for medical procedure as described in any one of (1)–(10), wherein the storage bottle is a product through blow molding with an aspect ratio of 20–60%,

(12) the discharging equipment for medical procedure as described in (11), wherein the storage bottle is the product made by blow molding with using a lopsided thickness parison (a standard plastic section member having generally a tubular shape usable in the blow molding), and the product made by blow molding is formed while a great thickness side of the lopsided thickness parison is arranged in a greater diameter direction of a flat cross sectional shape of the storage bottle,

(13) the discharging equipment for medical procedure as described in any one of (1)–(12), wherein a portable means for being fixed to clothing or the like is mounted on at least one of an upper portion of the storage bottle and the connector cap, and

(14) a discharging equipment set for medical procedure, including the discharging equipment for medical procedure as described in any one of (1)–(13), and elements usable in the Seldinger method such as the catheter and cannula needle to be retained in the body, the guide wire and the dilator or the like.

BRIEF EXPLANATION OF THE DRAWINGS

FIG. 2 is a front view showing a situation in which a connector cap is removed from a storage bottle of the discharging equipment for medical procedure as the embodiment of the invention, FIG. 3 is a view showing a situation in which a coupling device and a detachably connecting device of the discharging equipment for medical procedure as the embodiment of the invention are connected and a situation in which the coupling device and the detachably connecting device of the discharging equipment for medical procedure as the embodiment of the invention are disconnected.

BEST MODE FOR BRINGING THE INVENTION TO EFFECT

Figure 4:
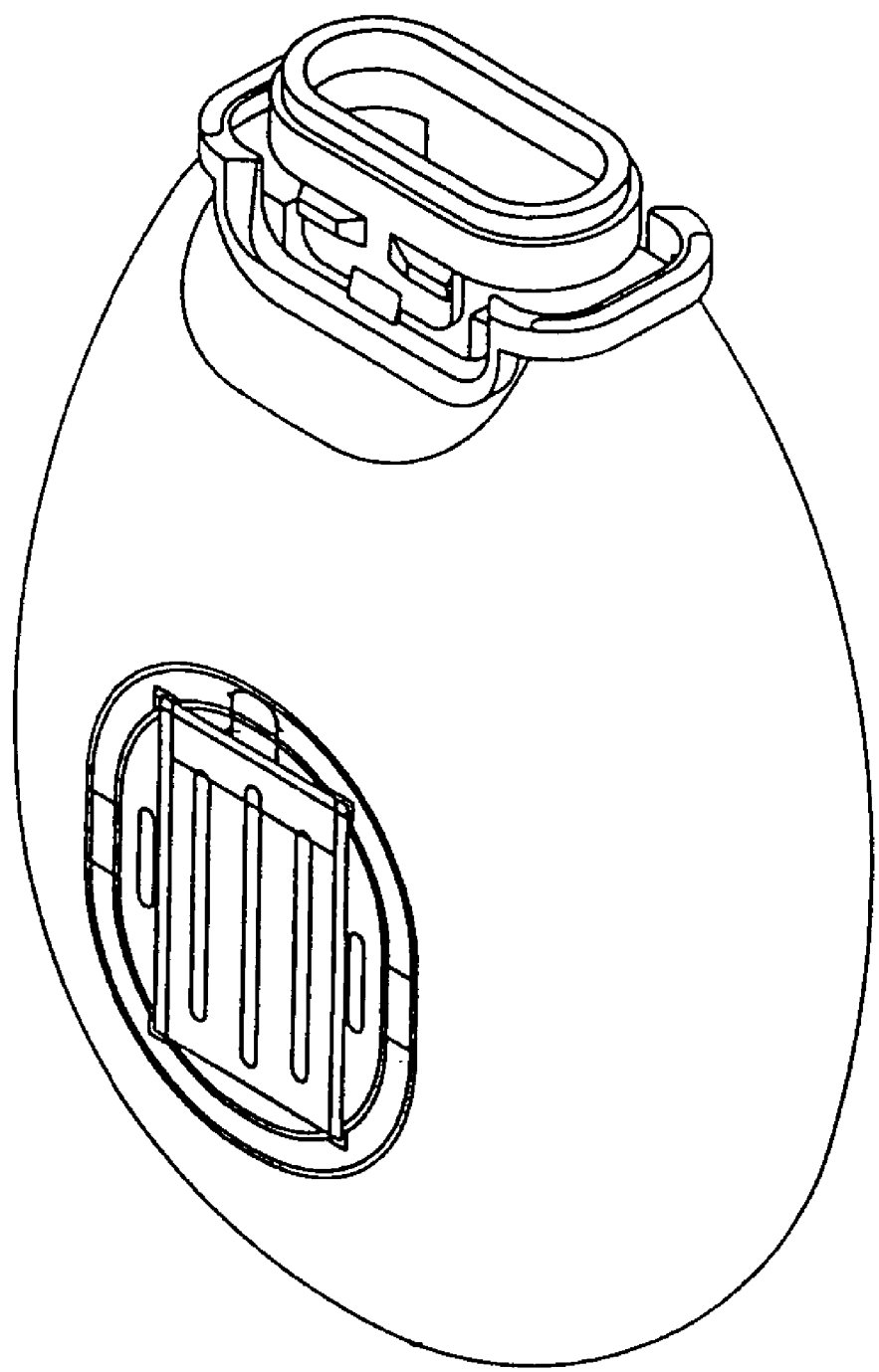
FIG. 4 is a perspective view of the storage bottle as the embodiment of the invention.
Figure 5:
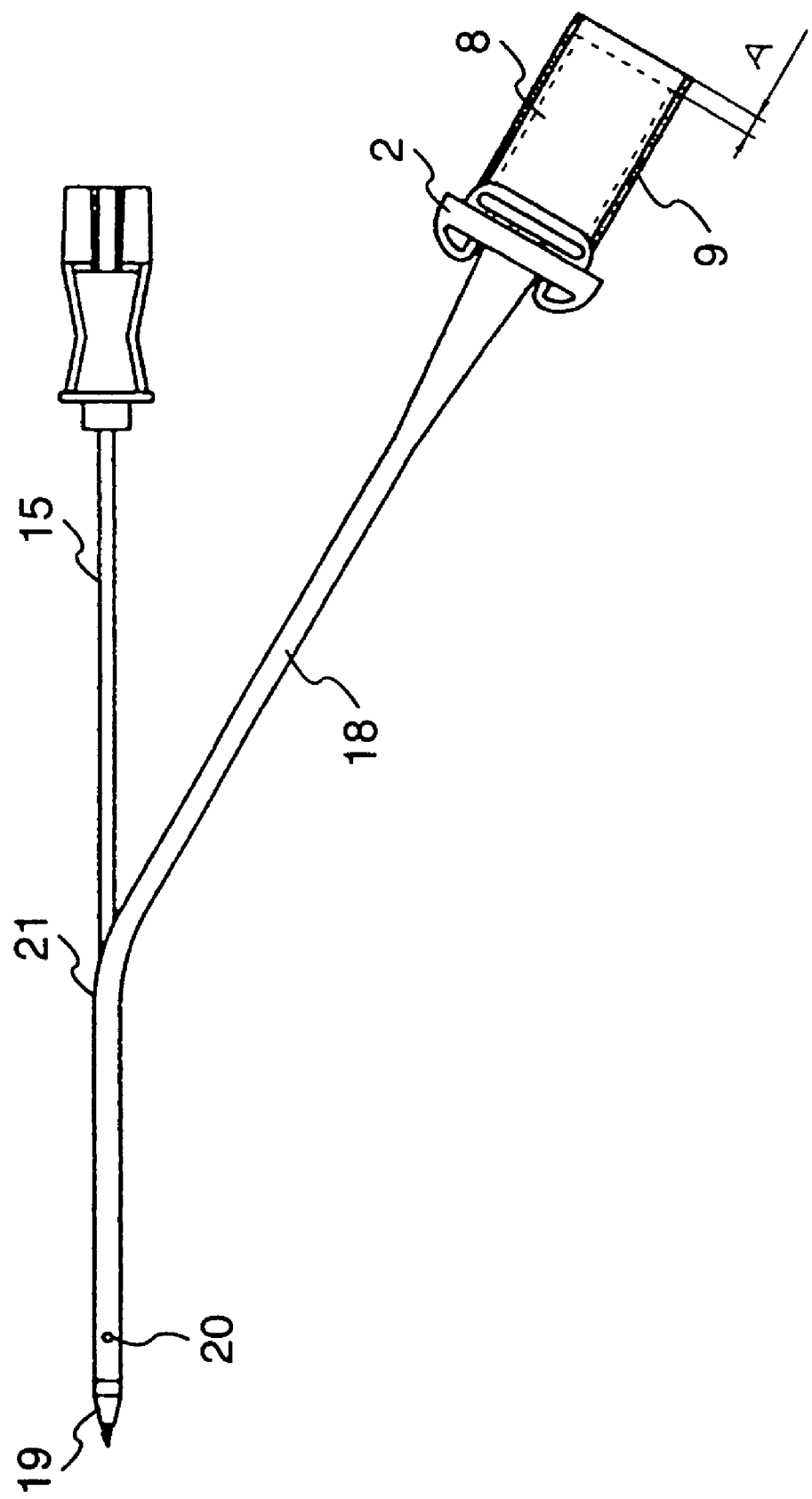
FIG. 5 is a front view showing a penetrating needle and a catheter in a discharging equipment for medical procedure as another embodiment of the invention.
Figure 6:
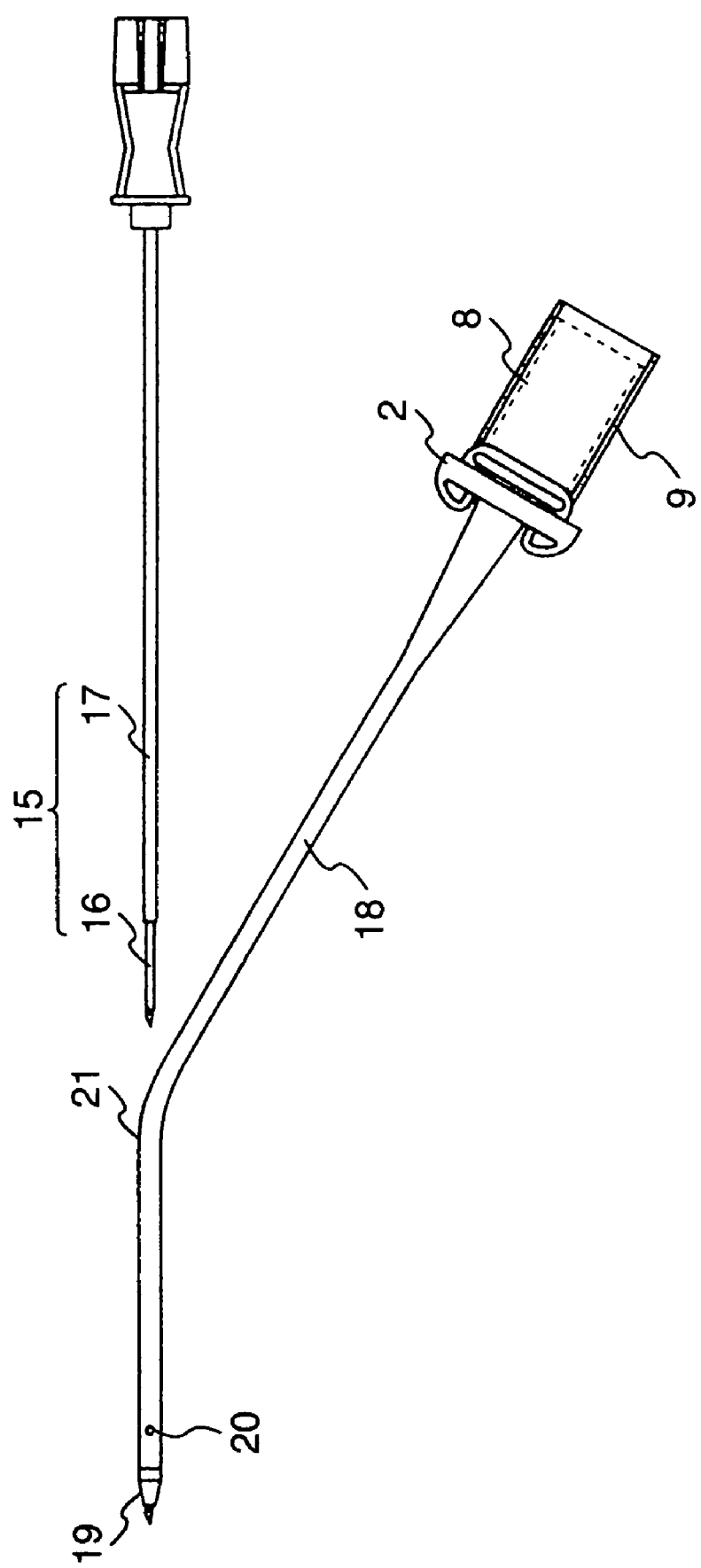
FIG. 6 is a front view showing a situation in which the penetrating needle is drawn out of the catheter in the discharging equipment for medical procedure as another embodiment of the invention.
Figure 7:
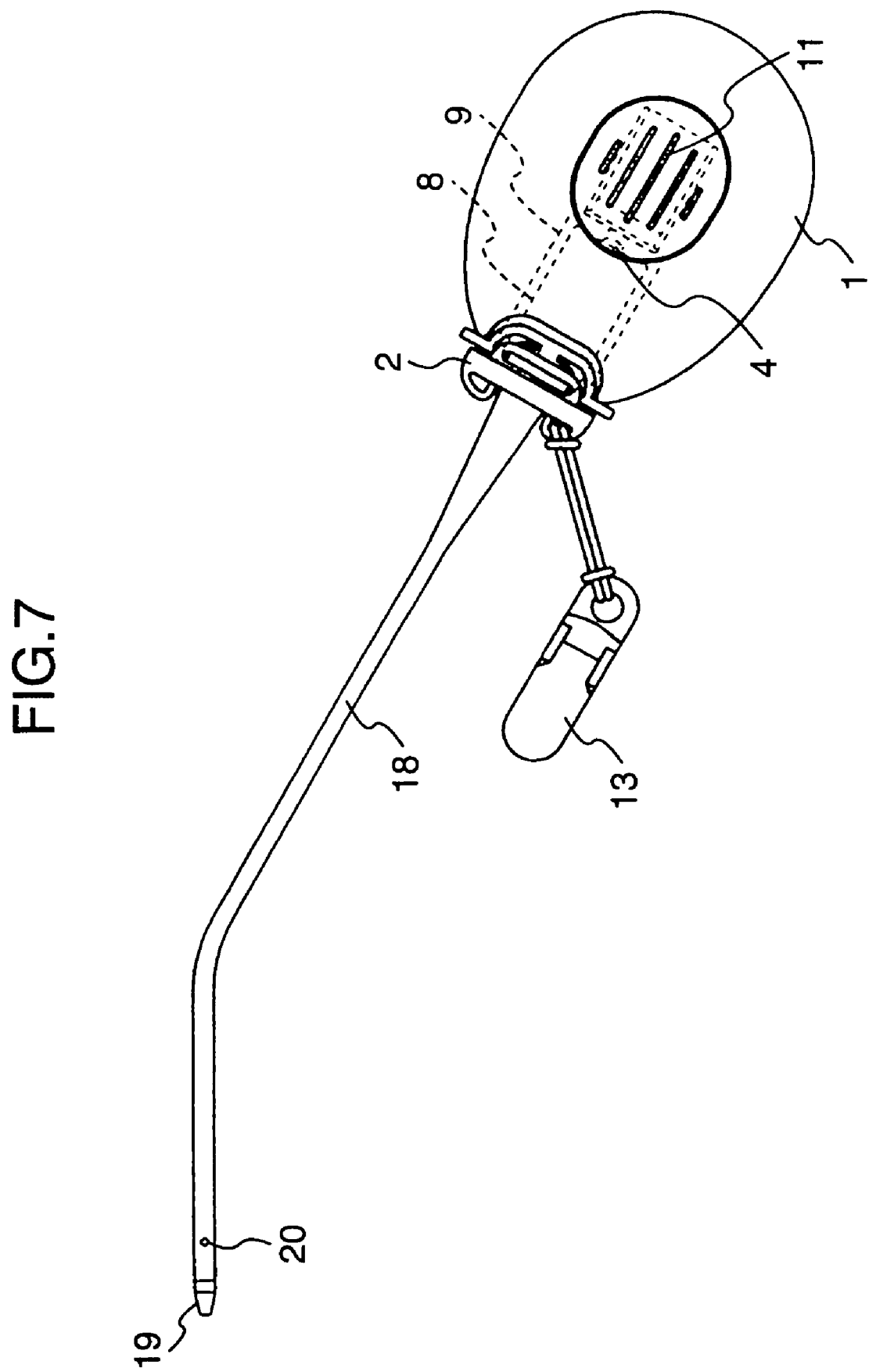
FIG. 7 is a front view showing a situation in which the storage bottle is connected to the catheter in the discharging equipment for medical procedure as the another embodiment of the invention.
Figure 8:
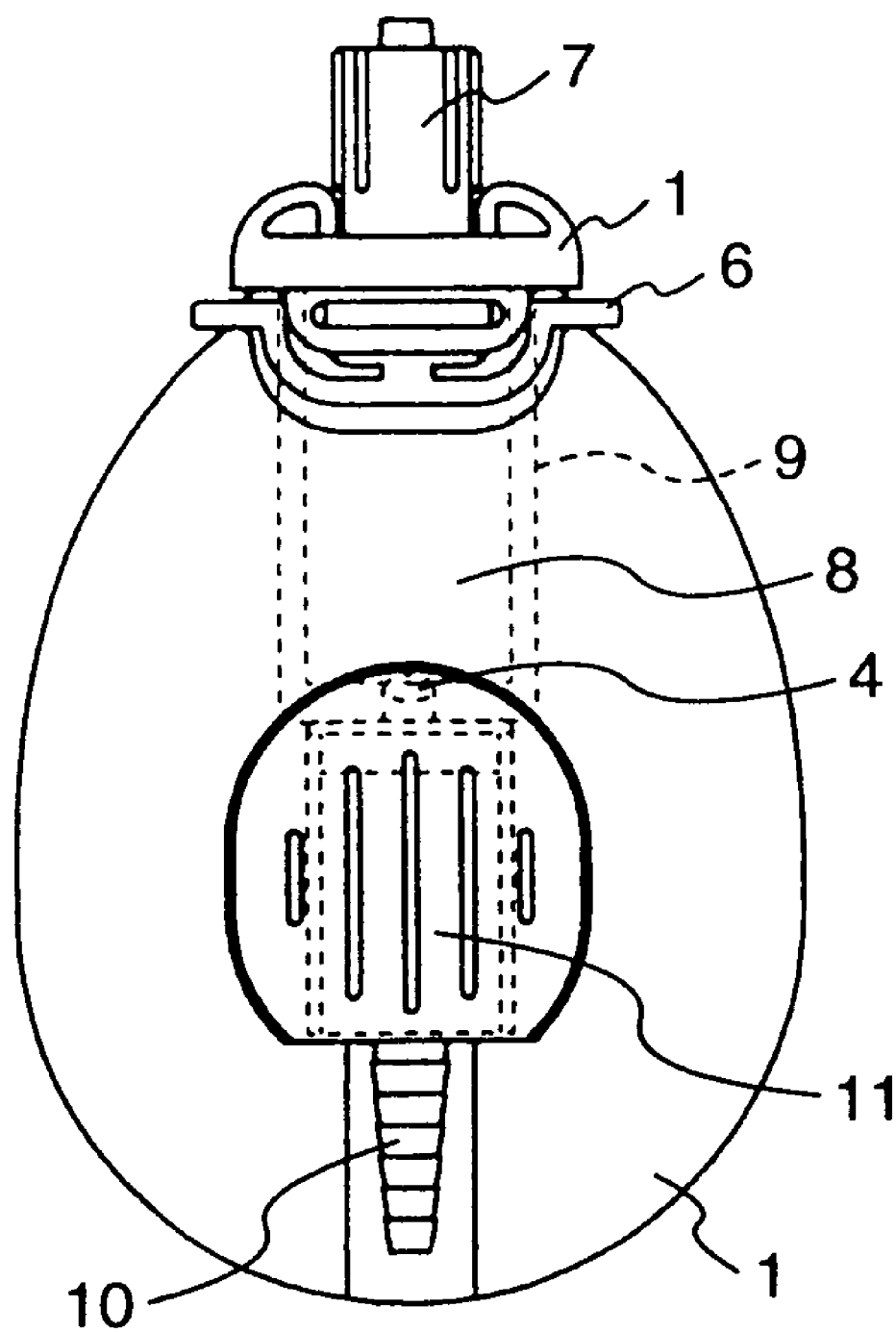
FIG. 8 is a front view showing a structure of a discharging equipment for medical procedure as another embodiment of the invention.
Figure 9:
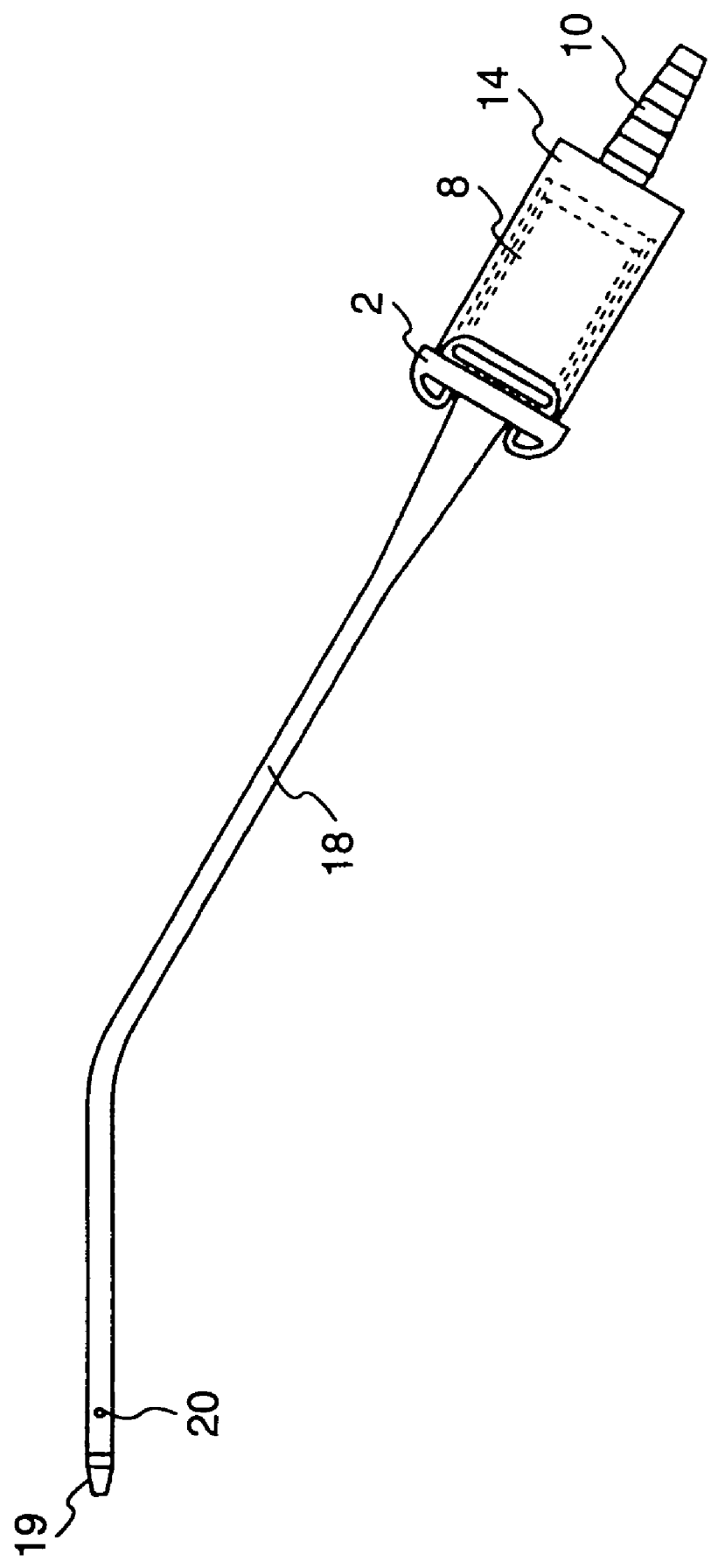
FIG. 9 is a front view showing a situation in which an adapter with a connecter is connected to the catheter in the discharging equipment for medical procedure as another embodiment of the invention.
Figure 10:
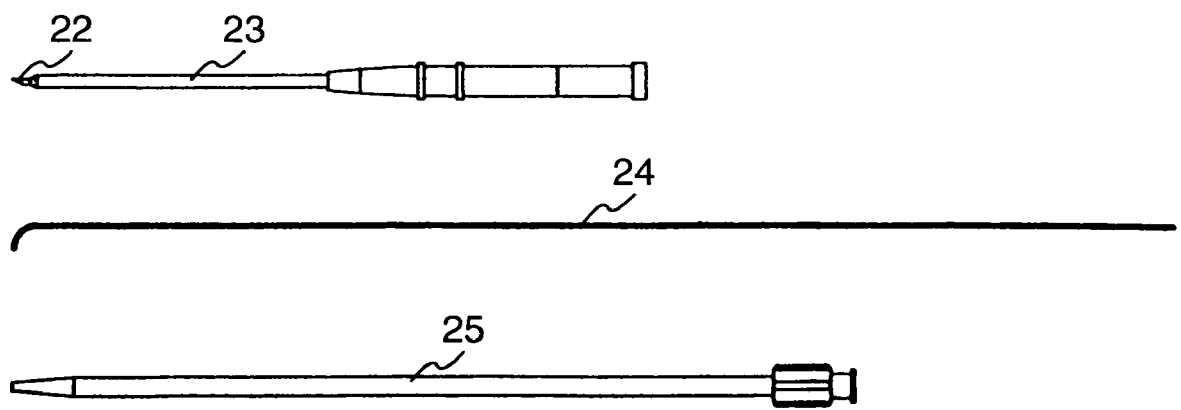
FIG. 10 is a front view showing a cannula needle, a guide wire and a dilator as other elements of the invention usable in the Seldinger method.

The invention is explained below in detail on the drawings. FIGS. 1–10 are views showing structures of discharging equipment for medical procedure as embodiments of the invention, FIG. 1 including a front view FIG. 1 (*a*) and a side view FIG. 1 (*b*) showing a situation in which a storage bottle and a connector cap are connected, wherein (a) is a front view and (b) is a side view, FIG. 2 is a view showing a situation in which the connector cap is removed from the storage bottle, FIG. 3 is a view showing a situation in which a coupling device and a detachably connecting device are connected and a situation in which the coupling device and the detachably connecting device are disconnected, FIG. 4 is a perspective view of the storage bottle, FIG. 5 is a view showing a situation in which a penetrating needle is inserted through a penetrating needle insert port of the catheter, FIG. 6 is a view showing a situation in which the penetrating needle is drawn out through the penetrating needle insert port of the catheter, FIG. 7 is a view showing a situation in which the storage bottle is connected to the catheter, FIG. 8 is a view showing another embodiment of the invention, FIG. 9 is a view showing a situation in which an adapter with a connector is connected to the catheter, and FIG. 10 is a view showing other elements of the invention usable in the Seldinger method.

Figure 1:
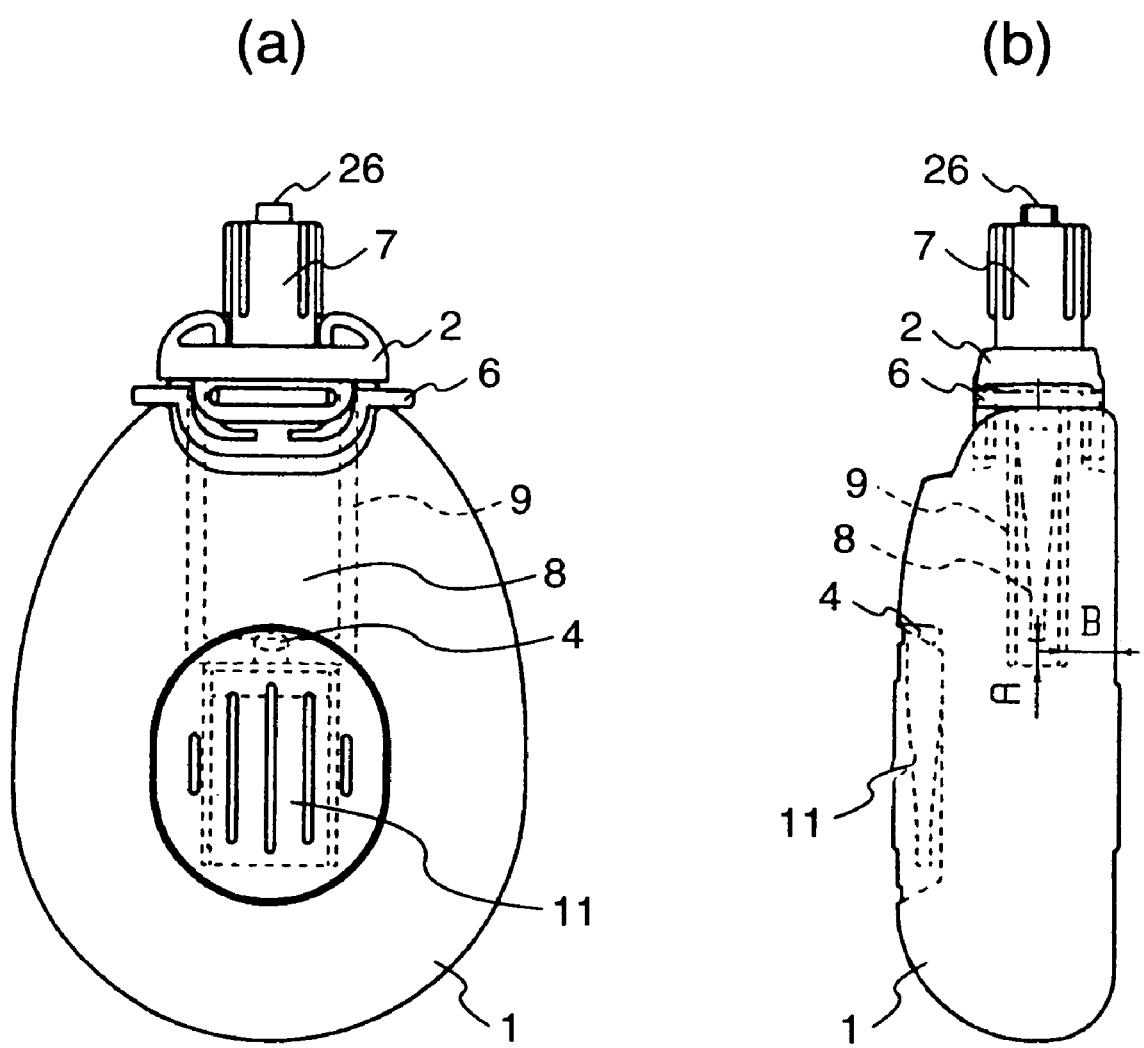
FIG. 1 shows a structure of a discharging equipment for medical procedure as an embodiment of the invention, wherein FIG. 1 (*a*) is a front view and FIG. 1 (*b*) is a side view.

As shown in FIGS. 1(*a*), 1(*b*) and 2, the storage bottle (1) has an inlet port (26), an outlet port (3) and a discharge port (4), and may have a scale for measuring an amount of discharged liquid on a side surface thereof if necessary. The inlet port (26) receives gas and liquid pooling in a chest cavity to be collected through a catheter into the storage bottle (1). The outlet port (3) discharges the stored liquid, and has preferably an opening area sufficient for exchanging the liquid to be discharged and an external air only through the outlet port (3) because the storage bottle (1) has no air relief root to form a closed system. A detachably connecting device (5) for a connector cap (2) is formed integrally on the outlet port (3), and may be a mechanism in which a coupling device (12) of the connector cap (2) is pressed upward to release a fitting (for example, a snap fitting) with the connecting device (5) by pressing left and right release levers (6) toward each other to be deformed as shown in FIG. 3, while the structure of the detachably connecting device (5) is not limited to this embodiment. The material of the detachably connecting device (5) may be hard vinyl chloride, ABS resin or the like for bearing a plurality of stress applying times.

The storage bottle (1) is preferably compact for improving portability and a flat container of aspect ratio 20–60% suitable for fitting onto a body surface, and is produced by a blow molding advantageous for producing cost. A product made by blow molding the storage bottle (1) will be explained in detail hereafter, it is important that a thickness of a flat cross section is made as constant as possible over the whole thereof so that the storage bottle (1) enables a pumping operation (recovery in shape in response to separation from a hand after being compressed) and a flash is prevented to the utmost from being formed on a mating face of the blow mold during the molding so that durability thereof for the pumping operation is kept. Generally, a parison having a relatively small diameter with respect to a traverse width of the product of molding is used to prevent the flash from being formed, but for the flat product of molding, a small diameter direction of the flat cross section thereof is set firstly in the mold to restrain an expansion of the resin so that the product of molding has a small thickness in a large diameter direction. Therefore, the parison has a difference in thickness and a large thickness side of the parison having the difference in thickness is arranged in a longitudinal direction of the flat shape of the storage bottle so that the thickness is constant.

Further, the material of the storage bottle (1) is preferably a plastic or rubber to obtain transparency for visibility of movement of the check valve and the condition of the discharged liquid and elasticity for pumping. The check valve B (11) has a flat tube shape of soft material such as plastic and rubber, and a front end at which inner surfaces thereof contact each other tightly in such a manner that gas flow discharged from the body can open the contact area to be discharged but prevent a reverse direction flow.

The connector cap (2) is detachably connectable to the outlet port (3) of the storage bottle (1), and has the coupling device (12) at a fitting portion thereof to form a pair with, for example, the outlet port (3) as described above so that a hermetic sealing is kept when being connected, while a preferable embodiment thereof has a packing therein to keep securely the hermetic sealing. The check valve A (8) openable toward the storage bottle (1) is mounted on the connector cap (2), and a connector A (7) connectable to the catheter (18) retained in the patient is mounted on an upper portion of the connector cap (2).

Further, in order to prevent contaminant bacteria from adhering to the check valve A (8) when the connector cap (2) is removed from the storage bottle (1), a protective cover (9) openable at a forward end side is mounted on an outside of the check valve A (8). Therefore, the check valve A (8) needs to be embedded entirely in the protective cover (9), and a front end position (A dimension in FIG. 1) is preferably lowered by not less than 5 mm. The check valve A (8) has the same structure as the above described check valve B (11), wherein the protective cover (9) is preferably made of hard material such as plastic, glass or the like to obtain the transparency for the visibility of the motion of the check valve A (8) and the protection of the check valve A (8).

An arrangement of the check valve A (8) of the connector cap (2) and the protective cover (9) with respect to the storage bottle (1) is described here in detail. In a basic case for consideration, the amount of the discharged liquid is small, and for further downsizing, the protective cover (9) including the check valve (8) is arranged in the storage bottle (1). While the protective cover (9) prevents the contaminant bacteria from adhering after the removal as described above, the front end of the check valve A (8) needs to be prevented by the protective cover (9) from being clogged by a contact between the check valve (8) and the discharged liquid pooling in the storage bottle (1), whereby the front end opening portion of the protective cover (9) needs to be arranged at a position where the contact with the discharged liquid is made as difficult as possible.

Therefore, for preventing the discharged liquid from flowing into the protective cover (9) when the discharged liquid is ascended upward on the side wall of the storage bottle (1) by the movement of the patient during carrying, it is preferable for a clearance to be formed between the inner wall of the storage bottle (1) and the protective cover (9). Further, since the storage bottle is carried by the patient as a general use condition, a bottom surface on FIG. 1 becomes an lower surface when the patient stands up, and a back surface becomes the lower surface when the patient lies. On the basis of this, the arrangement is determined from the outer dimension of the storage bottle (1) and an anticipated amount of the discharged liquid in such a manner that the contact is prevented in each case where the bottom surface on FIG. 1 is the lower surface and the case where the back surface is the lower surface when the anticipated amount of the discharged liquid is stored. Particularly, the distance (B dimension in FIG. 1) between the storage bottle (1) and the protective cover (9) is preferably made not more than 5 mm.

Further, it is preferable for improving the portability of the invention that various carrier means are incorporated, for example, a carrier clip mounted integrally or detachably on the upper portion of the storage bottle (1) or the connector cap (2), or an adhesive tape or the like attached to the back surface of the storage bottle (1) are usable in consideration of cost and operationality.

Further, an embodiment in which a connector B (10) for being coupled to a connection tube of the suction source for temporary low pressure continuous suction is mounted on a front end of the check valve B (11) of the discharge port (4) as shown in FIG. 8, or in which the connector cap (2) is detachably connectable to the adapter (14) with the connector B (10) through the same connecting means as the storage bottle (1) is preferable.

Next, a discharging equipment for medical procedure in which the catheter (18), the connector cap (2) and the check valve A (8) are integral with each other is explained. FIG. 5 shows that the penetrating needle (15) is inserted from the penetrating needle insert port (21) of the catheter (18), and FIG. 6 shows that the penetrating needle (15) is drawn out of the penetrating needle insert port (21) of the catheter (18). The penetrating needle (15) includes a double needle of an inner needle (16) and an outer tube needle (17) as metallic products of stainless steel or the like, although the materials thereof should not be limited specifically. A step between the inner needle (16) and the outer tube needle (17) is preferably 0.15–0.50 mm to abut on a front tip (19) of the catheter (18) and to prevent the penetrating needle (15) from projecting from the catheter (18). This is caused by the fact that when being less than 0.15–0.50 mm, there is a risk of that the penetrating needle (15) proceeds over the front tip (19) to penetrate the chest at a front of the needle when the penetrating needle (15) and the catheter (18) are inserted into the chest cavity. Further, when being more than 0.5 mm, the diameter of the catheter becomes large to cause a probability of a high damage for the patient. Practically, the dimension of the step is preferably 0.3 mm.

The catheter (18) has the penetrating needle insert port (21), and the integrally formed or X-ray impermeable front tip (19) is mounted on the front end of the catheter (18) so that the penetrating needle (15) is prevented by the step between the inner needle (16) and the outer tube needle (17) from projecting from the catheter (18). In the vicinity of the front end of the catheter (18), at least one side hole (20) opens to discharge efficiently the gas and liquid in the chest cavity, and on the back end of the catheter (18), the connector cap (2) including the check valve A (8) openable to the connecting side for the storage bottle (1) is mounted.

The penetrating needle insert port (21) is an insert port for inserting the penetrating needle (15) into the catheter (18), and the penetrating needle insert port (21) of a notch shape with a size for receiving the penetrating needle preferably has a dimension and shape for preventing resistance of the penetrating needle insert port (21) against withdrawal of the outer tube needle (17) when the catheter (18) is drawn out after the medical procedure while a length of the notch shape is preferably 1–10 mm. It is practically preferable that the length of the catheter (18) is 250–400 mm, and the outer diameter of the catheter (18) is 1–3 mm. The position of the penetrating needle insert port (21) is preferably 30–150 mm when taking a retaining length of the catheter (18) in the chest cavity into consideration. When being less than 30 mm, it is difficult for an adhering portion of the front tip (19) on the catheter (18) and a position of the side hole (20) to be maintained, and when being more than 150 mm, there is a risk that the atmospheric air proceeds into the chest cavity through the catheter (18).

Next, a method for using the discharge equipment for medical procedure of the invention is explained concretely. The skin on the penetrating portion is sanitized and after local anesthesia, cut shortly in accordance with a thickness of the catheter, and after retaining the catheter in the patient, the connector A (7) is connected to the terminating end of the catheter to complete the setting. Alternatively, after inserting the catheter (18) integrally including the connector cap (2) and the check valve A (8) to penetrate, the penetrating needle (15) is drawn out of the catheter (18), the front end of the catheter (18) is retained at an appropriate position in the chest cavity, and the connector cap (2) is connected to the outlet port (3) of the storage bottle (1) to finish the setting. In general, the above methods are usable, but for corpulent or child patients, the insertion with the Seldinger method (a catheter inserting method with using a guide wire) is preferable. At first, the cannula needle is inserted to penetrate. The guide wire (24) is inserted along a cannula envelope (23), and the cannula envelope (23) is drawn out. A dilator (25) is inserted along the guide wire (24) to enlarge the penetrating route. In a condition in which the dilator (25) is drawn out and the catheter (18) holds therein the outer tube needle (17) while the inner needle (16) is drawn out, the catheter (18) is inserted into the chest cavity along the guide wire (24). The retaining is finished by drawing out the outer tube needle (17) and the guide wire (24), and the connector cap (2) at the back end of the catheter (18) is connected to the outlet port (3) of the storage bottle (1).

When the liquid and gas in the chest cavity need to be discharged rapidly on setting, a compulsory discharge from the chest cavity can be performed by pumping the storage bottle to open and close alternately the check valve A (7) and the check valve B (11). When the discharged liquid such as pleural effusion or the like pools in the storage bottle (1), release levers (9) of the detachably connecting device (5) are pressed inward toward each other to be deformed to remove the connector cap (2) so that the discharged liquid is discharged from the outlet port (3). In this time, the atmospheric air is prevented from proceeding into the chest cavity through the check valve A (8) attached to the connector cap (2).

INDUSTRIAL APPLICABILITY

The discharge equipment for medical procedure of the invention is more compact particularly for cases of small discharged liquid, in which an manual discharge operation can be performed without additional necessary equipment, and the atmospheric air is prevented by the check valve arranged on the back end of the catheter to open only toward the exterior from proceeding into the chest cavity when the penetrating needle is drawn out, so that it is usable as a low cost simple equipment.

The invention claimed is:

1. A discharging equipment for medical procedure, comprising a connector cap and a storage bottle configured to be detachably connected to each other, wherein a connector configured to be connected to a catheter configured to be retained in a patient, a check valve configured to be opened only to a storage bottle side and having an outer periphery covered by a protective cover, and a coupling device configured to be connected to the storage bottle are mounted on the connector cap, and the storage bottle is a hollow container having an outlet port and a discharge port, a detachably connecting device configured to be connected to the connecting cap is mounted on the outlet port, and a check valve configured to be opened only in an outward direction of the storage bottle is arranged at the discharge port, wherein the storage bottle is elastic configured to enable the storage bottle to return to its original state in response to a release from a hand after being compressed so that the discharging is carried out by a manual pumping operation, wherein the detachable connecting device of the storage bottle and the outlet are included by an integrally formed element with a release lever, and the storage bottle and the connector cap are detachably connected to each other with a release of the connecting device of the connector cap by the release lever.

2. A discharging equipment for medical procedure according to claim 1, wherein when the connector cap is connected to the outlet port of the storage bottle, the protective cover of the check valve mounted on the connector cap is arranged in the storage bottle while being prevented from contacting an inner wall of the storage bottle, and a distance between the inner wall at a back face of the storage bottle and the protective cover is not less than 5 mm.

3. A discharging equipment for medical procedure according to claim 1, wherein a connector to be connected to a suction source is mounted on an outlet of the check valve at the discharge port.

4. A discharging equipment for medical procedure according to claim 1, wherein an adapter with the connector to be connected to the suction source is detachably connectable to a check valve side of the connector cap.

5. A discharging equipment for medical procedure according to claim 1, wherein the storage bottle is made of an elastic body.

6. A discharging equipment for medical procedure according to claim 1, wherein the storage bottle is a product through blow molding with an aspect ratio of 20–60%.

7. A discharging equipment for medical procedure according to claim 6, wherein the storage bottle is formed by blow molding using a parison of lopsided thickness, and the product formed by blow molding is formed while the side of said parison having the greatest thickness is arranged in a greater diameter direction of a flat cross sectional shape of the storage bottle.

8. A discharging equipment for medical procedure according to claim 1, wherein a portable means for being fixed to clothing is mounted on at least one of an upper portion of the storage bottle and the connector cap.

9. A discharging equipment set for medical procedure, comprising the discharging equipment for medical procedure according to claim 1, and elements usable in the Seldinger method.

10. A discharging equipment for medical procedure according to claim 1, wherein a connector to be connected to a suction source is mounted on an outlet of the check valve at the discharge port.

11. A discharging equipment for medical procedure according to claim 1, wherein the storage bottle is made of an elastic body.

12. A discharging equipment for medical procedure according to claim 1, wherein the storage bottle is produced by blow molding with an aspect ratio of 20–60%.

13. A discharging equipment for medical procedure according to claim 1, wherein a portable means for being fixed to clothing is mounted on at least one of an upper portion of the storage bottle and the connector cap.

14. A method for using the equipment of claim 1, comprising sanitizing the skin of a patient, applying local anesthesia, opening a passage through the skin in accordance with a thickness of a catheter, positioning the catheter in the patient, connecting the inlet port of said equipment to the terminating end of the catheter and then drawing out fluids from the patient.

15. A discharging equipment according to claim 9, wherein said elements comprise a catheter and cannula needle to be retained in a body, a guide wire or a dilator.

* * * * *